United States Patent [19]

Rei

[11] Patent Number: 4,933,011

[45] Date of Patent: Jun. 12, 1990

[54] ANTIMICROBIAL SOLUTION

[75] Inventor: Nuno M. Rei, Boxford, Mass.

[73] Assignee: Morton Thiokol, Inc., Chicago, Ill.

[21] Appl. No.: 560,761

[22] Filed: Dec. 12, 1983

[51] Int. Cl.$^5$ .............................................. A01N 9/00
[52] U.S. Cl. ................................. 106/18.31; 514/709;
523/122; 524/126; 524/128; 71/86
[58] Field of Search ............... 252/399; 424/145, 237,
424/19–25; 106/18.31; 604/890; 524/126, 128;
523/122; 514/709

[56] References Cited

U.S. PATENT DOCUMENTS

| | | |
|---|---|---|
| Re. 29,409 | 9/1977 | Yeager ................................. 424/78 |
| 3,052,597 | 9/1982 | Johnston ............................... 167/22 |
| 3,199,990 | 8/1965 | Taylor ................................... 106/15 |
| 3,471,571 | 10/1969 | Harvey ................................ 206/607 |
| 4,049,822 | 9/1977 | Rei et al. ............................. 424/297 |
| 4,363,663 | 12/1982 | Hill ..................................... 106/18.31 |

Primary Examiner—Barry S. Richman
Assistant Examiner—T. J. Wallen
Attorney, Agent, or Firm—Gerald K. White

[57] ABSTRACT

An antimicrobial solution of a microbiologically active organo sulfonyl ethylene, isoindole dicarboximide or zinc hydroxypyridine thionate dissolved in an organo phosphorus compound selected from the group consisting of organophosphites and organophosphonates.

24 Claims, No Drawings

ANTIMICROBIAL SOLUTION

BACKGROUND OF THE INVENTION

1. Field of the Invention

This invention relates to antimicrobial compositions containing organo sulfonyl ethylene compounds and more particularly to antimicrobial solutions of organo sulfonyl ethylene compounds that are compatible with plastic polymers.

This invention further relates to antimicrobial compositions containing antimicrobial compounds selected from the group consisting of isoindole dicarboximides having a sulfur atom bonded to the nitrogen atom of the dicarboximide group, and zinc hydroxy-pyridine thionates. More particularly, this invention relates to antimicrobial solutions of antimicrobial compounds selected from the group consisting of isoindole dicarboximides having a sulfur atom bonded to the nitrogen atom of the dicarboximide group and zinc hydroxy-pyridine thionates, said antimicrobial solutions being compatible with plastic polymers.

2. Description of the Prior Art

To protect polymer compositions from attack by fungi and similar organisms, it is normal to add an antimicrobial compound to the polymeric composition. One class of antimicrobial compounds is organo sulfonyl ethylene compounds. These compounds are disclosed in U.S. Pat. Nos. 3,052,597; 3,199,990 and 3,471,571. The latter patent is directed to a process for preparing the compounds and the former two patents disclose the compound's utility as fungicides.

Many of the available microbiocidal materials are solid and, in order to incorporate them homogeneously in the resin composition, it is necessary first to mix them with a liquid which solubilizes or disperses the material uniformly and thereafter, mixing the liquid composition with the resin. Unfortunately, the solubility of many of the microbiologically active material in the common solvent materials is quite low. Therefore, it is either difficult to incorporate a sufficiently high concentration of the microbiocidal material with the resin or, if sufficiently high concentrations of the active material can be incorporated in the resin, an undesirably high concentration of the solvent also must be incorporated in the resin with the resultant deterioration of the desirable characteristics of the resin composition.

The same difficulty encountered with many of the more readily available antimicrobials in adding them to plastic polymers has been encountered with the organo sulfonyl ethylene compounds. The problem is an incompatibility that results in a poor blending manifested by what has been described as "blooming" and generally a tendency to separate with the biocide moving to the surface and causing surface defects and loss of the biocide.

One method of solving this problem of the incompatibility of the biocide and polymer is to solubilize the biocide in a solvent to form a biocidal solution which is compatible with the polymer. Thus, for example, Reissue Pat. No. 29,409 (reissue of U.S. Pat. No. 3,288,674) discloses that microbiocidal properties can be imparted to vinyl resins by the incorporation therein of a selected phenoxarsine compound dissolved in a solvent selected from phenols and monocarboxylic acids. Likewise, U.S. Pat. No. 4,049,822 discloses microbiocidal solutions for resins including a glycyl phosphite or glycyl phosphonate and a microbiologically active phenoxarsine compound. The microbiocidal solutions disclosed in Re. 29,409 and U.S. Pat. No. 4,049,822 may also include additional solvents, dispersants or resin plasticizers.

SUMMARY OF THE INVENTION

In accordance with this present invention it has been found that organo sulfonyl ethylene compounds can be dissolved in organo phosphorus compounds to form stable solutions. These solutions have been found compatible with plastic polymers and may be blended with them either directly or after first being diluted with suitable plastic modifiers. Thus it is an object of the invention to provide a solution of organo sulfonyl ethylene compounds with organo phosphorus compounds as antimicrobial additives for plastic polymers.

Also in accordance with the invention it has been found that antimicrobial compounds selected from the group consisting of isoindole dicarboximides having a sulfur atom bonded to the nitrogen atom of the dicarboximide group, and zinc hydroxy-pyridine thionates can be dissolved in organo phosphorus compounds to form stable liquid solutions. These solutions have been found to be compatible with plastic polymers and can be blended with them either directly or after first being diluted with suitable plastic modifiers. Thus it is an object of the invention to provide a solution of antimicrobial compounds selected from isoindole dicarboximides having a sulfur atom bonded to the nitrogen atom of the dicarboximide groups, and zinc hydroxy-pyridine thionates with organo phosphorous compounds as antimicrobial additives for plastic polymers.

Other objects and features of the invention will become apparent upon reading the following disclosure.

DESCRIPTION OF THE PREFERRED EMBODIMENTS

The antimicrobial organo sulfonyl ethylenes useful in the compositions of this invention are organic compounds containing at least one carbon-carbon double bond with a sulfonyl group bonded directly to one or both of the carbon atoms in the carbon-carbon double bond. Thus, the organo sulfonyl ethylenes contain at least one group having the structure:

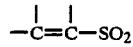

or the structure:

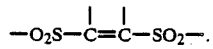

The carbon-carbon double bond in the organo sulfonyl ethylene compound may be part of an alkene chain, a cycloalkene ring or a carbocylic or heterocyclic aromatic ring.

Preferred organo sulfonyl ethylenes wherein the carbon-carbon double bond is part of an alkylene chain have the following formulas:

$$RSO_2CH\!=\!CHSO_2R \qquad (I)$$

$$Q_1SO_2CH\!=\!CHSO_2Q_2 \qquad (II)$$

In the above formula (I) R is an alkyl group of 1 to 12 carbon atoms and wherein the compound has the trans configuration. In formula (II) $Q_1$ and $Q_2$ are selected from the group consisting of alkyl having 1 to 12 carbon atoms, phenyl, biphenyl, benzyl, lower alkyl phenyl, chlorophenyl, bromophenyl and nitrophenyl.

The preferred organo sulfonyl ethylene compound according to formulas (I) and (II) is trans -1, 2-bis(n-propyl sulfonyl) ethylene.

A preferred organo sulfonyl ethylene wherein the carbon-carbon double bond is part of an aromatic ring is 2,3,5,6-tetrachloro -4-(methylsulfonyl) pyridine having the structure:

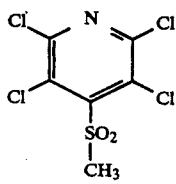
(III)

The antimicrobial compounds useful in the compositions of this invention which are isoindole dicarboximides having a sulfur atom bonded to the nitrogen atom of the dicarboximide group contain at least one group having the structure:

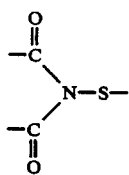
(IV)

The preferred isoindole dicarboximides according to formula (IV) are the following:

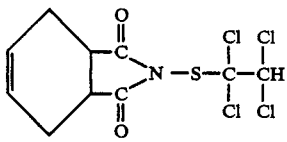
(V)

bis-N-[(1,1,2,2,-tetrachloroethyl)thio]-4-cyclohexene-1,2,-dicarboximide

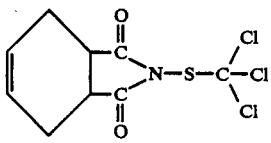
(VI)

N-trichloromethylthio-4-cyclohexene-1,2-dicarboximide

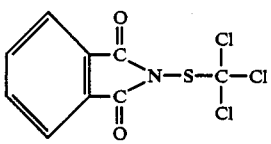
(VII)

N-trichloromethylthio phthalimide

The zinc hydroxy-pyridine thionates useful in the compositions of this invention preferably have the structure:

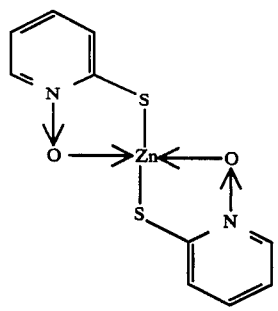
(VIII)

bis[1-hydroxy-2(1H)-pyridinethionato-O,S]-(T-4)-zinc

The liquid organo phosphorus solvents encompassed by the present invention are alkyl phosphites, aryl phosphites, alkyl-aryl phosphites, mono, di, tri and polyphosphites as well as glycol phosphonates. Alkyl phosphites include dioctyl phosphite, triiodecyl phosphites, triisoctyl phosphites, trilauryl phosphite, tris (dipropylene glycol) phosphite and phosphites based on 2,2,4-trimethyl -1,3-pentane diol. Aryl phosphites include diphenyl phosphite, trisnonyl phenyl phosphite, and triphenyl phosphite. Alkyl-aryl phosphites include diphenyl isodecyl phosphite, diphenyl isooctyl phosphite and phenyl diisodecyl phosphite. Diphosphites include bis-(neopentylglycol) triethylene glycol diphosphite, tetrakis (nonylphenyl) polypropylene glycol diphosphite and tetraphenyl dipropylene glycol diphosphite. Tri-and polyphosphites include heptakis (dipropylene glycol) triphosphite and poly(dipropylene glycol) phenyl phosphite. By glycol phosphonate is meant bis(-dipropylene glycol) dipropylene glycol phosphonate and di(amyl) amyl phosphonate. These organo phosphorous compounds can be employed in admixture.

The organo sulfonyl ethylene-, isoindole dicarboximide-or zinc hydroxy-pyridine thionate-organo phosphite; or organo sulfonyl ethylene-, isoindole dicarboximide-or zinc hydroxy-pyridine thionateorgano phosphonate solutions are incorporated into polymeric compositions as such or they can be diluted with plasticizers or other modifiers such that the biocide-solvent or biocide-solvent-diluent solutions contain organo sulfonyl ethylene, isoindole dicarboximide or zinc hydroxy-pyridine thionate in amounts of about 2 weight percent to about 10 weight percent. The biocide-solvent or biocide-solventdiluent solutions are incorporated into polymeric compositions in amounts of about 1 weight percent to about 15 weight percent, preferably about 1 weight percent to about 10 weight percent, so that the resulting polymeric composition contains about 0.01 weight percent to about 2.0 weight percent, preferably about 0.1 weight percent to about 2.0 weight percent, more preferably about 0.1 weight percent to about 1.0 weight percent, still more preferably about 0.15 weight percent to about 1.0 weight percent and more preferably about 0.5 weight percent organo sulfonyl ethylene, isoindole dicarboximide or zinc hydroxy-pyridine thionate.

The organo sulfonyl ethylene, isoindole dicarboximide and zinc hydroxy-pyridine thionate solutions of the present invention can be employed in coatings, adhesives, and a variety of polymeric compositions such as polyvinyl chloride, vinyl chloride-vinyl acetate copolymer, ethylene vinyl acetate or with polyethylene, polypropylene or polyurethane. They are also valuable in highly dilute solutions as biocidal sprays or baths wherein the organo sulfonyl ethylene, dicarboximide or zinc hydroxy-pyridine thionate is present in percentages substantially less than 1.0 weight percent.

In a preferred embodiment, this invention provides an antimicrobial solution comprising a microbiologically active organo sulfonyl ethylene dissolved in an organo phosphorus compound selected from the group consisting of organo phosphites and organo phosphonates.

In another preferred embodiment, this invention provides an antimicrobial solution comprising a microbiocidally active organo sulfonyl ethylene dissolved in an organophosphous compound selected from the group consisting of heptakis (dipropyleneglycol) triphosphite, triisodecyl phosphite, tris neodal phosphite, trisdipropylene glycol phosphite and diphenyl isodecyl phosphite.

In another preferred embodiment, this invention provides an antimicrobial solution comprising a microbiologically active organo sulfonyl ethylene dissolved in an organo phosphorus compound selected from the group consisting of heptakis (dipropyleneglycol) triphosphite, triisodecyl phosphite, tris neodal phosphite, trisdipropylene glycol phosphite and diphenyl isodecyl phosphite, wherein the organo sulfonyl ethylene is trans-1,2-bis(n-propyl sulfonyl)ethylene.

In another preferred embodiment, this invention provides an antimicrobial solution comprising a microbiologically active organo sulfonyl ethylene dissolved in an organo phosphorus compound selected from the group consisting of heptakis (dipropyleneglycol) triphosphite, triisodecylphosphite, tris neodal phosphite, trisdipropylene glycol phosphite and diphenyl isodecyl phosphite, wherein the organo sulfonyl is represented by one of the formulae: $RSO_2CH=CHSO_2R$, $Q_1SO_2CH=CHSO_2Q_2$, wherein R is an alkyl group of 1 to 12 carbon atoms and wherein the compound has the trans configuration and wherein $Q_1$ and $Q_2$ are selected from the group consisting of alkyl having 1 to 12 carbon atoms, phenyl, biphenyl, benzyl, lower alkyl phenyl, chlorophenyl, bromophenyl and nitrophenyl.

In another preferred embodiment, this invention provides an antimicrobial solution comprising a microbiologically active organo sulfonyl ethylene dissolved in an organo phosphorus compound selected from the group consisting of organo phosphites and organo phosphonates, wherein the organo sulfonyl ethylene is represented by one of the formulae: $RSO_2CH=CHSO_2R$, $Q_1SO_2CH=CHSO_2Q_2$, wherein R is an alkyl group having 1 to 12 carbon atoms and wherein the compound has the trans configuration and wherein $Q_1$ and $Q_2$ are selected from the group consisting of alkyl having 1 to 12 carbon atoms, phenyl, biphenyl, benzyl, lower alkyl phenyl, chlorophenyl, bromophenyl and nitrophenyl.

In another preferred embodiment, this invention provides an antimicrobial solution comprising a microbiologically active organo sulfonyl ethylene dissolved in an organo phosphorus compound selected from the group consisting of organo phosphites and organo phosphonates mixed with a plastic modifier wherein the modifier is at least 10 percent by weight.

In another preferred embodiment, this invention provides an antimicrobial solution comprising a microbiologically active organo sulfonyl ethylene dissolved in an organo phosphorus compound selected from the group consisting of organo phosphites and organo phosphonates mixed with a plastic modifier wherein the modifier is at least 10 percent by weight and is a plasticizer.

In another preferred embodiment, this invention provides an antimicrobial solution comprising a microbiologically active organo sulfonyl ethylene dissolved in an organo phosphorus compound selected from the group consisting of organo phosphites and organo phosphonates mixed with a plastic modifier wherein the modifier is at least 10 percent by weight and is a plasticizer selected from the group consisting of phthalate esters and epoxidized oils.

In another preferred embodiment, this invention provides an antimicrobial solution comprising a microbiologically active organo sulfonyl ethylene dissolved in an organo phosphorus compound selected from the group consisting of organo phosphites and organo phosphonates wherein said organo sulfonyl ethylene is at least 3 percent by weight of the solution.

The following examples illustrate the present invention and are not intended to limit the same.

EXAMPLES 1-15

The compositions in Table I were prepared by mixing the specified organo phosphite or organo phosphonate with the specified biocide. The resulting mixture was then heated with stirring at ambient condition until a clear solution resulted. The resulting solution was then allowed to cool to room temperature.

TABLE I

| EXAMPLE NO. | SOLUTION COMPONENT | WEIGHT PERCENT | SOLUTION APPEARANCE |
| --- | --- | --- | --- |
| 1 | trans-1,2,-bis (n-propyl sulfonyl) ethylene[a] | 10 | Soluble, but slightly hazy |
|  | poly(dipropylene glycol) phenyl phosphite[b] | 90 |  |
| 2 | trans-1,2,-bis(propyl sulfonyl) ethylene | 10 | Soluble, but slightly hazy |
|  | bis(dipropylene glycol) dipropylene glycol phosphonate[c] | 90 |  |
| 3 | trans-1,2,bis(n-propyl sulfonyl) ethylene | 33⅓ | Soluble, but precipitated after standing overnight |

TABLE I-continued

| | | | |
|---|---|---|---|
| | bis(dipropylene glycol) phosphonate | 66⅔ | |
| 4 | trans-1,2,-bis(n-propyl sulfonyl) ethylene | 33⅓ | Soluble, slightly hazy, viscous |
| | phosphite based on 2,2,4-trimethyl-1,3-pentane diol[d] | 66⅔ | |
| 5 | Compound III[e] | 30 | Clear |
| | bis(dipropylene glycol) dipropylene glycol phosphonate | 70 | |
| 6 | Compound III | 20 | Clear, amber |
| | bis(dipropylene glycol) dipropylene glycol phosphonate | 80 | |
| 7 | Compound III | 30 | Clear |
| | tridecyl phosphite | 70 | |
| 8 | Compound III | 35 | Red-amber |
| | triisodecyl phosphite[f] | 65 | |
| 9 | Compound III | 25 | Clear |
| | poly(dipropyleneglycol) phenyl phosphite[g] | 75 | |
| 10 | Compound III | 30 | Dark amber, slight crystallization after 8 hrs. |
| | poly(dipropyleneglycol) phosphite | 70 | |
| 11 | Compound VI | 25 | Clear |
| | poly(dipropyleneglycol) phenyl phosphite | 75 | |
| 12 | Compound VI | 10 | Clear |
| | diisooctyl phosphite | 40 | |
| | poly(dipropyleneglycol) phenyl phosphite | 50 | |
| 13 | Compound V[i] | 20 | Clear, yellow |
| | poly(dipropyleneglycol) phosphite | 80 | |

| EXAMPLE NO. | SOLUTION COMPONENT | WEIGHT PERCENT | APPEARANCE |
|---|---|---|---|
| 14 | N-trichloromethylthio phthalimide[j] | 15 | Slightly hazy |
| | diisooctyl phosphite | 42.5 | |
| | poly(dipropyleneglycol) phenyl phosphite | 42.5 | |
| 15 | Compound VIII[k] | 15 | |
| | diisooctyl phosphite | 42.5 | |
| | di(propyleneglycol) phenyl phosphite | 42.5 | |

[a] sold under the trademark Vancide PA by R. T. Vanderbilt Co., Inc.
[b] sold under the trademark Weston DHOP by Borg-Warner Corporation
[c] sold under the trademark Weston DPGP by Borg-Warner Corporation
[d] sold under the trademark Weston CDP-1129 by Borg-Warner Corporation
[e] 2,3,5,6,-tetrachloro-4-(methylsulfonyl) pyridine
[f] sold under the trademark Weston TOP by Borg-Warner Corporation
[g] sold under the trademark Weston DHOP by Borg-Warner Corporation
[h] N-trichloromethylthio-4-cyclohexene-1,2-dicarboximide sold under the trademark Vancide 89 by R. T. Vanderbilt Co., Inc.
[i] cis-N-[(1,1,2,2-tetrachloroethyl)thio)]-4-cyclohexene-1,2-dicarboximide sold under the trademark Difolatan by Chevron Chemical Co.
[j] sold under the trademark Fungitrol-11 by Chevron Chemical Co.
[k] bis[1-hydroxy-2(1H)-pyridinethionato-O,S]-(T-4)-zinc sold under the trademark Zinc Omadine by Olin Corp.

EXAMPLES 16–22

The compositions in Table II, which contain a biocide, phosphite or phosphonate and a plastic modifier, were prepared by dissolving the biocidal compound in the specified phosphite or phosphonate as described in Examples 1–15 and blending the resulting solution with the specified plastic modifier.

TABLE II

| EXAMPLE NO. | COMPONENT | WEIGHT PERCENT |
|---|---|---|
| 16 | Compound III | 15 |
| | poly(dipropyleneglycol) phenyl phosphite | 35 |
| | dioctyl phthalate | 50 |
| 17 | Compound III | 15 |
| | poly(dipropyleneglycol) phenyl phosphite | 35 |
| | epoxidized soybean oil | 50 |
| 18 | Compound III | 15 |
| | poly(dipropyleneglycol) phenyl phosphite | 35 |
| | diisodecyl phthalate | 50 |
| 19 | Compound III | 25 |
| | bis(dipropylene | 25 |

TABLE II-continued

| EXAMPLE NO. | COMPONENT | WEIGHT PERCENT |
|---|---|---|
| | glycol) | |
| | dipropylene glycol phosphonate | |
| | dipropylene glycol dibenzoate | 75 |
| 20 | Compound VI | 1 |
| | diisooctyl phosphite | 4 |
| | poly(dipropylene glycol) phenyl phosphite | 5 |
| | dioctyl phthalate | 90 |
| 21 | N-trichloromethylthio phthalimide | 1.5 |
| | diisooctylphosphite | 4.25 |
| | poly(dipropylene glycol) phenyl phosphite | 4.25 |
| | dioctyl phthalate | 90 |
| 22 | Compound VIII | 1.5 |
| | diisooctyl phosphite | 4.25 |
| | poly(dipropylene glycol) phenyl phosphite | 4.25 |
| | dioctyl phthalate | 90 |

While dioctyl phthalate, diisodecyl phthalate and epoxidized soybean oil are specified in Table II, these are members of the groups phthalate esters and epoxidized oils, respectively. Other members of these groups have similar properties as plasticizers and can be expected to be equally suitable for the present use. Likewise, while dipropylene glycol dibenzoate is specified in Table II, it is a member of the group glycol diesters. Other members of this group have similar properties as plasticizers and can be expected to be equally suitable for the present use.

The solutions prepared in the foregoing examples are effective in inhibiting the growth of microorganisims and are, therefore, antimicrobial solutions.

While the invention has been described with respect to specific examples, it is obvious to use other related chemical compositions known to have similar characteristics for the same purposes and it is intended to cover the invention as set forth in the following claims.

I claim:

1. An antimicrobial solution comprising a microbiologically active organo sulfonyl ethylene dissolved in an organo phosphorus compound selected from the group consisting of organo phosphites and organo phosphonates.

2. An antimicrobial solution according to claim 1 wherein the organo phosphorus compared is selected from the group consisting of heptakis (dipropyleneglycol) triphosphite, triisodecyl phosphite, tris neodal phosphite, trisdipropylene glycol phosphite, and diphenyl isodecyl phosphite.

3. An antimicrobial solution according to claim 2 wherein the organo sulfonyl ethylene is trans-1,2,-bis (n-propyl sulfonyl) ethylene.

4. An antimicrobial solution according to claim 2 wherein the organo sulfonyl ethylene is represented by one of the formulae: $RSO_2CH=CHSO_2R$, $Q_1SO_2CH=CHSO_2Q_2$, wherein R is an alkyl group of 1 to 12 carbon atoms and wherein the compound has the trans configuration and wherein $Q_1$ and $Q_2$ are selected from the group consisting of alkyl having 1 to 12 carbon atoms, phenyl, biphenyl, benzyl, lower alkyl phenyl, chlorophenyl, bromophenyl and nitrophenyl.

5. An antimicrobial solution according to claim 1 wherein the organo sulfonyl ethylene is represented by one of the formulae: $RSO_2CH=CHSO_2R$, $Q_1SO_2CH=CHSO_2Q_2$, wherein R is an alkyl group of 1 to 12 carbon atoms and wherein the compound has the trans configuration and wherein $Q_1$ and $Q_2$ are selected from the group consisting of alkyl having 1 to 12 carbon atoms, phenyl, biphenyl, benzyl, lower alkyl phenyl, chlorophenyl, bromophenyl and nitrophenyl.

6. An antimicrobial solution according to claim 1 mixed with a plastic modifier wherein the modifier is at least 10 percent by weight.

7. An antimicrobial solution according to claim 6 wherein said plastic modifier is a plasticizer.

8. An antimicrobial solution according to claim 7 wherein said plasticizer is selected from the group consisting of phthalate esters and epoxidized oils.

9. An antimicrobial solution according to claim 7 wherein said plasticizer is a glycol diester.

10. An antimicrobial solution according to claim 1 wherein said organo sulfonyl ethylene is at least 3 percent by weight of the solution.

11. An antimicrobial solution according to claim 1 wherein said organo sulfonyl ethylene is 2,3,5,6,-tetrachloro-4-(methylsulfonyl) pyridine.

12. An antimicrobial solution according to claim 10 mixed with a plastic modifier.

13. An antimicrobial solution according to claim 12 wherein the plastic modifier is a plasticizer.

14. An antimicrobial solution according to claim 13 wherein the plasticizer is selected from the group consisting of phthalate esters, epoxidized oils and glycol diesters.

15. An antimicrobial solution comprising a microbiologically active isoindole dicarboximide having a sulfur atom bonded to the nitrogen atom of the dicarboximide group dissolved in an organophosphorus compound selected from the group consisting of organo phosphites and organo phosphonates.

16. An antimicrobial solution according to claim 15 wherein said isoindole dicarboximide is selected from the group consisting of bis-N-[(1,1,2,2,-tetrachloroethyl)thio]-4-cyclohexene-1,2-dicarboximide; N-trichloromethylthio-4-cyclohexene -1,2-dicarboximide and N-trichloromethylthio phthalimide.

17. An antimicrobial solution according to claim 15 mixed with a plastic modifier.

18. An antimicrobial solution according to claim 17 wherein said plastic modifier is a plasticizer.

19. An antimicrobial solution according to claim 18 wherein the plasticizer is selected from the group consisting of phthalate esters, epoxidized oils and glycol diesters.

20. An antimicrobial solution comprising a microbiologically active zinc hydroxy-pyridine thionate dissolved in an organophosphorus compound selected from the group consisting of organo phosphites and organo phosphonates.

21. An antimicrobial solution according to claim 20 wherein the zinc hydroxy-pyridine thionate is bis[1-hydroxy-2(1H)-pyridinethionato-O,S]-(T-4)-zinc.

22. An antimicrobial solution according to claim 20 mixed with a plastic modifier.

23. An antimicrobial solution according to claim 22 wherein the plastic modifier is a plasticizer.

24. An antimicrobial solution according to claim 23 wherein the plasticizer is selected from the group consisting of phthalate esters, epoxidized oils and glycol diesters.

* * * * *